United States Patent [19]

Bruna

[11] Patent Number: 5,568,884
[45] Date of Patent: Oct. 29, 1996

[54] PORTABLE DEVICE FOR PROJECTING MEASURED QUANTITIES OF A FLUID SUBSTANCE BY MEANS OF A PUFF OF COMPRESSED AIR

[75] Inventor: Pascal Bruna, Rouen, France

[73] Assignee: Valois S.A., Le Neubourg, France

[21] Appl. No.: 491,927

[22] PCT Filed: Jan. 12, 1994

[86] PCT No.: PCT/FR94/00035

§ 371 Date: Sep. 13, 1995

§ 102(e) Date: Sep. 13, 1995

[87] PCT Pub. No.: WO94/15716

PCT Pub. Date: Jul. 21, 1994

[30] Foreign Application Priority Data

Jan. 14, 1993 [FR] France .................... 93 00309

[51] Int. Cl.⁶ ............................. B67D 5/58
[52] U.S. Cl. ............... 222/189.09; 222/365; 222/636; 239/307; 406/132; 128/203.13
[58] Field of Search ............. 222/189.09, 189.11, 222/263, 280, 361, 365, 635, 636, 637, 518, 559; 128/203.15, 203.13, 203.19; 239/307, 310, 318, 351; 406/122, 132

[56] References Cited

U.S. PATENT DOCUMENTS

| | | | |
|---|---|---|---|
| 2,581,182 | 1/1952 | Fields | 128/203.15 |
| 2,587,215 | 2/1952 | Priestly | 222/361 |
| 4,524,769 | 6/1985 | Wetterlin | 128/203.15 |
| 5,033,463 | 7/1991 | Cocozza | 128/203.15 |
| 5,113,855 | 5/1992 | Newhouse | 128/203.12 |
| 5,239,992 | 8/1993 | Bougamount et al. | 128/203.15 |
| 5,447,151 | 9/1995 | Bruna et al. | 128/203.15 |

FOREIGN PATENT DOCUMENTS

| | | |
|---|---|---|
| 79478 | 5/1983 | European Pat. Off. . |
| 166294 | 1/1986 | European Pat. Off. . |
| 0473965 | 3/1992 | European Pat. Off. . |
| 9204068 | 3/1992 | WIPO . |
| 92/05823 | 4/1992 | WIPO . |

*Primary Examiner*—Andres Kashnikow
*Assistant Examiner*—Philippe Dergkshani
*Attorney, Agent, or Firm*—Sughrue, Mion, Zinn, Macpeak & Seas

[57] ABSTRACT

A device for projecting measured quantities of a fluid substance by a puff of compressed air, said device comprising: a body (1) having an ejection channel (4); an actuator member (2) displaceable relative to the body (1) between a rest position and an actuated position; a resilient return member (19) urging the actuator member (2) towards its rest position; a supply (3) of said substance; a feed (5, 6) adapted to move a measured quantity of said substance from the supply (3) into the ejection channel (4); and an air pump (7) comprising a pump chamber (8) having an inlet valve (10, 11) in communication with the atmosphere; the device being characterized in that the outlet valve is constituted by a valve piston (12) constrained to be displaced with the actuator member (2) and sliding in sealed manner in a valve cylinder (13) having a top end (13a), said cylinder having a lateral outlet orifice (14) which communicates with the ejection channel (4), said valve cylinder having its top end (13a) in communication with the pump chamber (8), said lateral outlet orifice being positioned sufficiently far from said top end (13a) of the valve cylinder for the valve piston (12) to isolate the lateral outlet orifice (14) from the pump chamber so long as the actuator member (2) is not in the immediate vicinity of its actuated position.

7 Claims, 6 Drawing Sheets

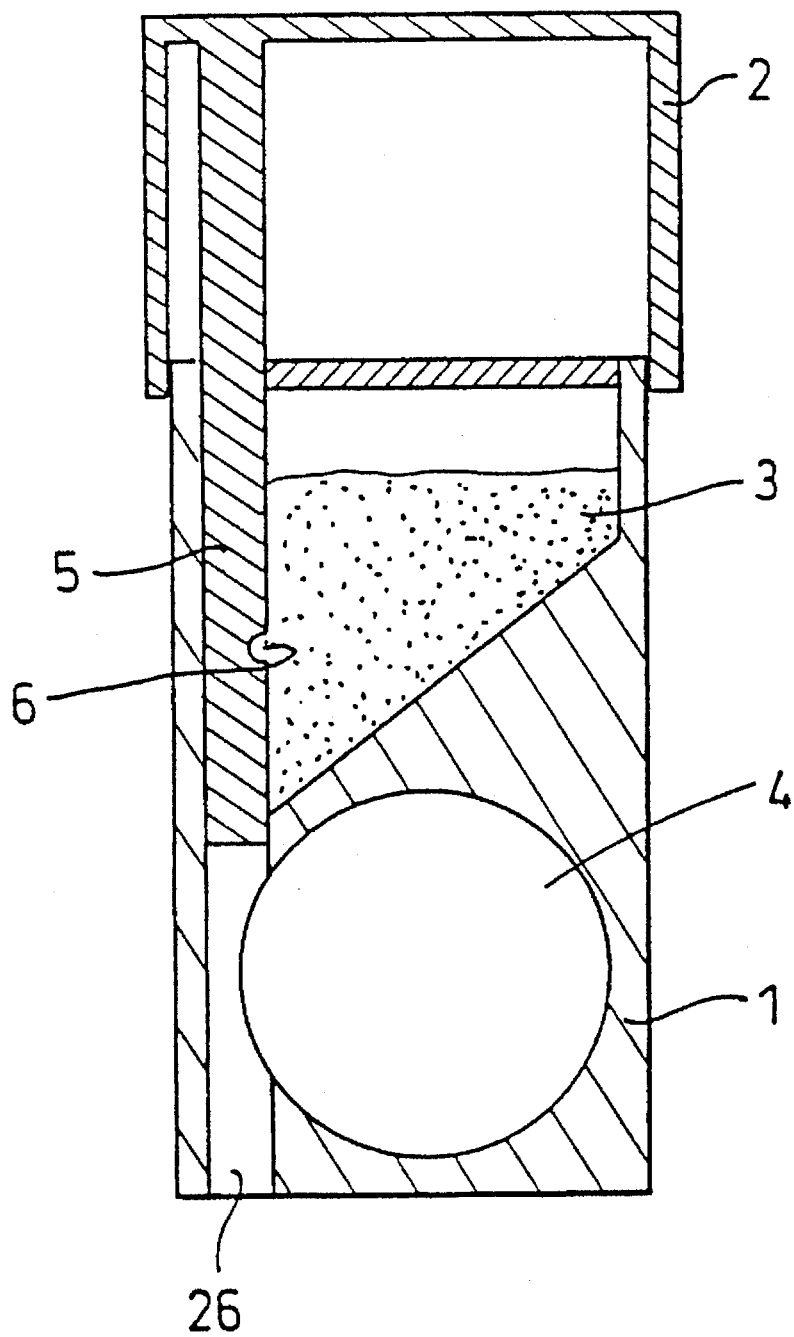

PORTABLE DEVICE FOR PROJECTING MEASURED QUANTITIES OF A FLUID SUBSTANCE BY MEANS OF A PUFF OF COMPRESSED AIR

The present invention relates to a portable device for projecting measured quantities of a fluid substance by means of a puff of compressed air.

The intended fluid substances are particularly powders, but also possibly liquids.

The present invention is particularly applicable to the field of sprays for projecting doses of a pharmaceutical substance in powder form onto the mucous membranes of the respiratory tract (by mouth or by nose). Such sprays use an effect whereby the powder is projected onto the mucous membrane, unlike inhalers for sending powder into the bronchi, where the powder is transported by the flow of air inhaled by the patient on breathing.

It is known to use aerosol sprays for this purpose. The powder is contained in a tank with a liquefied propellant gas, and a valve triggers expulsion of the powder in suspension in the liquefied gas. On expanding at atmospheric pressure, the liquefied gas returns to the gaseous state and expands very greatly, thereby propelling the powder.

However, aerosols suffer from the drawback of using propellant gases that are generous either for the environment (freons) or else for users (hydrocarbons). Also, before expelling powder, they require the tank to be properly shaken in order to put the powder into suspension in the liquefied gas. If a user forgets to shake the tank, or shakes it insufficiently, then the expelled dose of powder is inaccurate.

An object of the present invention is to remedy those drawbacks.

The present invention provides a device for projecting measured quantities of a fluid substance by means of a puff of compressed air, said device comprising:

a body having an ejection channel;

an actuator member displaceable relative to the body between a rest position and an actuated position;

a resilient return member for the actuator member, urging the actuator member towards its rest position;

a supply of said substance;

feed means adapted to displace a measured quantity of said substance from the supply into the ejection channel when the actuator member is displaced from its rest position to its actuated position; and an air pump having a pump chamber provided with a displaceable wall secured to the actuator member and adapted to compress the pump chamber when the actuator member is displaced from its rest position to its actuated position, said pump chamber having an inlet valve which communicates with the atmosphere, and an outlet valve which communicatees with the ejection channel, the outlet valve being constituted by a shutter member which co-operates with an outlet opening, said shutter member isolating the outlet opening from the pump chamber so long as the actuator member is not in the immediate vicinity of its actuated position, said shutter member opening communication between the pump chamber and the outlet opening when the actuator member is in the immediate vicinity of its actuated position;

the device being characterized in that the outlet valve is constituted by a valve piston constrained to move with the actuator member and sliding in sealed manner in a valve cylinder having a top end, said cylinder having a lateral outlet orifice which communicates with the ejection channel, said valve cylinder having its top end in communication with the pump chamber, said lateral outlet orifice being positioned sufficiently far from said top end of the valve cylinder for the valve piston to isolate the lateral outlet orifice from the pump chamber so long as the actuator member is not in the immediate vicinity of its actuated position.

In an embodiment of the invention, the valve cylinder may possess a vent orifice positioned in such a manner that said lateral outlet orifice is disposed between said vent orifice and said top end of the valve cylinder which is in communication with the pump chamber. In this case, said vent orifice may optionally be provided with a filter to prevent dust penetrating into the valve cylinder.

According to another characteristic of the invention, the feed means are constituted by a feed rod having a measuring recess at an intermediate position along its length, the feed rod not being secured to the actuator member, said feed rod being urged towards an abutment position by resilient means and the actuator member travelling along a certain stroke from its rest position before pushing said rod against the action of the resilient means of the feed rod.

Examples of measured quantity feed devices having a moving member provided with one or more measuring recesses are given in the following documents: WO-A-92 05823, EP-A-0 069 715 (and the corresponding American patent U.S. Pat. No. 4,524,769), GB-A-2 041 763, EP-A-0 166 294, GB-A-2 165 159, EP-A-0 079 478, U.S. Pat. No. 2,587,215, and U.S. Pat. No. 2,581,182.

In a particular embodiment, the measuring recess is annular in shape and is located within the ejection channel when the actuator member is in its actuated position.

In an advantageous embodiment, the feed rod slides in the supply of substance to be projected, said supply is an enclosure that slides with lost motion parallel to the feed rod in a housing of the body, resilient means urging said enclosure away from the ejection channel, the enclosure possessing a wall remote from the ejection channel, which wall includes an orifice through which the feed rod passes, the feed rod including a lateral projection that is outside the enclosure when the actuator member is in its rest position, said lateral projection interfering with said wall of the enclosure by displacing the enclosure a certain distance against the urging of the resilient means of the enclosure when the actuator member is displaced towards its actuated position, and said lateral projection is sufficiently flexible to retract resiliently as it passes through said orifice of said wall of the enclosure once sufficient axial force is exerted by said lateral projection on said wall of the enclosure. A device for feeding a measured quantity of powder and having a feed rod and a sliding enclosure is already known from document WO-A-92 05823.

In a variant, and said wall of the enclosure which is remote from the ejection channel is sufficiently flexible to deform elastically so as to allow the lateral projection of the feed rod to pass through the orifice of said wall when sufficient axial force is exerted by said lateral projection on said wall of the enclosure.

Other characteristics and advantages appear from the detailed description of an embodiment of the invention given by way of non-limiting example, with reference to the accompanying drawings.

In the drawings:

FIG. 3a is a detailed view showing a variant of the device of FIG. 1;

FIG. 6 is a diagrammatic view in vertical cross-section through a variant of the device of FIG. 5.

In the various figures, portions that are identical or similar are designated by the same references.

The device of the invention can generally be made using parts molded out of plastics material, with the exception of the springs which are generally made of metal, and the seals or gaskets which are generally made of elastomer material. In the description below, the materials from which the various parts of the device of the invention are therefore generally not described, except when such materials present particularities.

Figure 1:
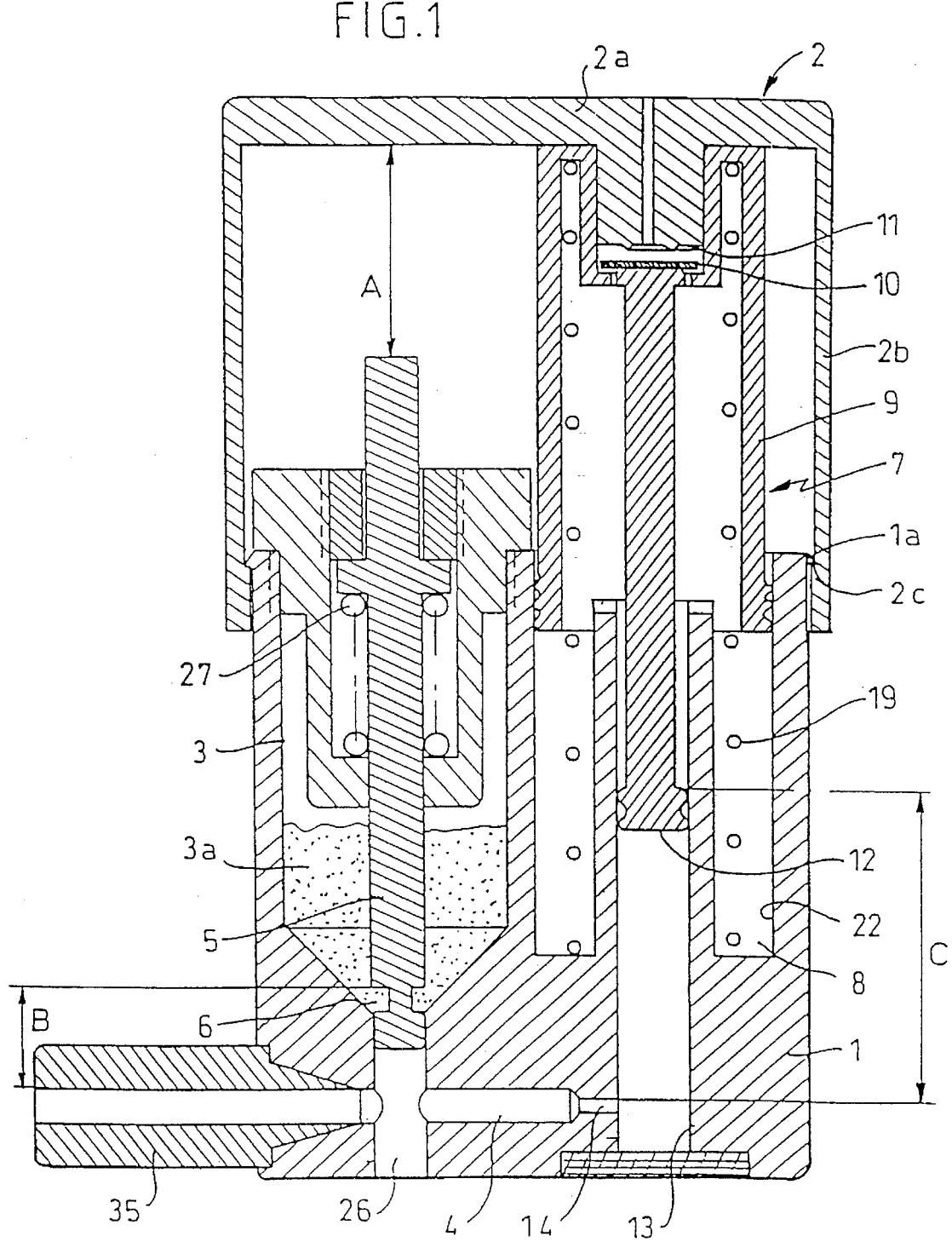
FIG. 1 is a longitudinal vertical section view of a first embodiment of the device of the invention.

With reference to FIG. 1, the device of the invention is externally in the form of a housing suitable for being held in the hand. The housing comprises a body 1 and a cap or pusher 2 that covers the body 1 and that slides axially relative to the body 1 between a rest position, as shown in FIG. 1, and an actuated position in which the pusher 2 is moved as close as possible to the body 1. A return spring 19 urges the pusher 2 towards its rest position.

The cap or pusher 2 includes a horizontal top wall 2a, and a vertical side wall 2b which extends downwards to an end having an inside rim 2c. The inside rim 2c cooperates with external projections or studs 1a that prevent the side wall 2a from releasing the body 1 under drive from the return spring 19. The rim 2c and the projections 1a thus define the rest position of the pusher 2.

The body 1 includes a supply 3 of substance to be projected in a puff of compressed air. In the example shown in FIG. 1 said substance is a power 3a, which is the most usual case, even though it is also possible to project a liquid with the device of the invention.

The body 1 also includes an ejection channel 4 and an endpiece 35 which extends the ejection channel beyond the body 1. The endpiece 35 may be of various different shapes depending on the use for which the device is intended, e.g. spraying a powder into the noise or into the mouth.

In addition, the device of FIG. 1 includes feeder means which are described in detail below, and which are adapted to move one dose of powder from the supply 3 to the ejection channel 4 when the pusher is moved from its rest position to its actuated position.

Finally, the device includes an air pump 7 whose outlet communicates with the ejection channel 4 and which is adapted to send a puff of compressed air into said channel 4 when the pusher 2 reaches its actuated position.

Figure 2:
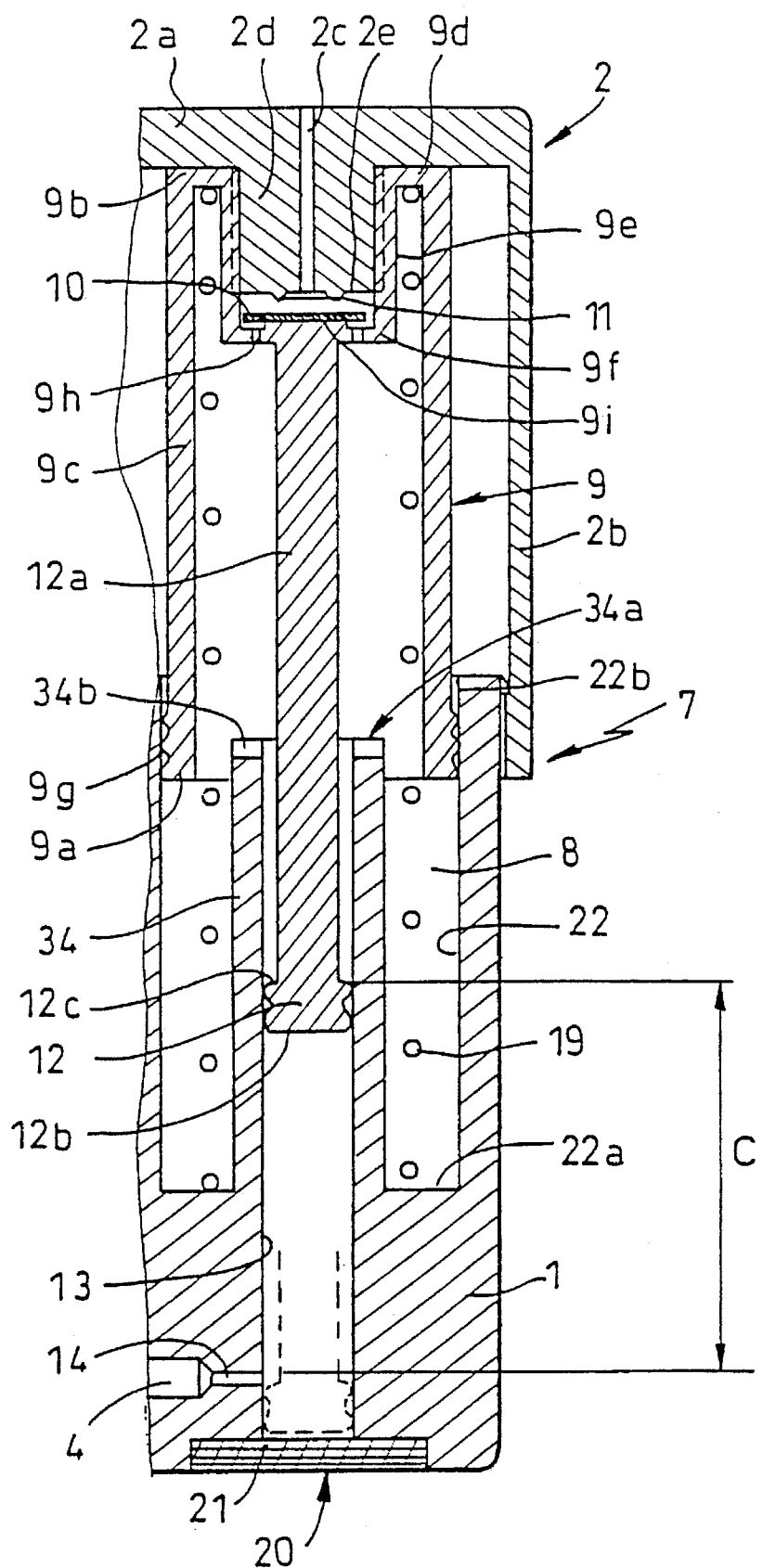
FIG. 2 is a fragmentary view showing the righthand portion of FIG. 1.

As shown in greater detail in FIG. 2, the air pump 7 of the FIG. 1 device includes a pump cylinder 22 formed in the body 1, said pump cylinder 22 extending vertically between a bottom 22a and an open top end 22b close to the pusher 2. The pump 7 also includes a pump piston 9 which slides in sealed manner inside the pump cylinder 22, the cylinder 22 and the piston 9 together defining a pump chamber 8 that is filled with air.

In the example shown in FIG. 2, the pump piston 9 is tubular. The pump piston 9 has an outer cylindrical wall 9c which extends between a bottom end 9a and a top end 9b. The bottom end 9a advantageously includes one or more peripheral sealing lips 9g which slide in sealed manner inside the pump cylinder 22. The top end 9b of the cylindrical wall 9c extends radially inwards by means of an annular rim 9d which itself extends radially inwards in the form of a cup constituted by an inside cylindrical wall 9e that extends vertically downwards from the rim 9d to a central web 9f. The top wall 2a of the pusher 2 includes a cylindrical portion 2d which extends vertically downwards to an end face 2e. The cylindrical portion 2d is engaged inside the inner cylindrical wall 9e of the piston, these two parts being fixed to each other by a force-fit or by any other means. As shown in FIG. 2, the cylindrical portion may optionally be threaded on the outside while the inner cylindrical wall 9e of the piston is threaded on the inside, so the two parts are screwed together. After assembly, the annular rim 9d of the piston is in abutment against the top wall 2a of the pusher, and a space is left empty between the web 9f and the end face 2e. The pusher 2 includes an air inlet hole 2c which is pierced vertically through the center of the cylindrical portion 2d and which opens out both to the atmosphere and into the space that exists between the web 9f and the end face 2e.

In addition, the web 9f includes a raised portion 9i together with one or more orifices 9h that cause the space between the web 9f and the end face 2e to communicate with the pump chamber 8. In addition, the end face 2e of the cylindrical portion 2d includes a valve seat 11 that may be in the form of an annular fillet surrounding the opening of the hole 2c in the face 2e. Finally, a valve member 10, which may be a disk of elastomer material, is trapped in the space between the web 9f and the end face 2e. The diameter of the valve member 10 is less than the inside diameter of the cylindrical wall 9e. Thus, the valve member 10 and the valve seat 11 form an inlet non-return valve for the pump, enabling air to penetrate into the pump chamber 8 when suction is created inside said pump chamber 8, and preventing air from escaping from said pump chamber 8 when said pump chamber is under pressure, since the valve member 10 is then pressed against the valve seat 11 in airtight manner.

The return spring 19 of the pusher 2 which has already been referred to above is mounted between the bottom 22a of the pump cylinder and the annular rim 9b of the pump piston.

The body 1 also includes an inner cylindrical wall 34 that is concentric with the pump cylinder 22 and that extends vertically upwards in the center of the pump cylinder 22 from the bottom 22a of the cylinder 22 up to a top end 34a. The end 34a advantageously includes one or more radial notches 34b. The cylindrical wall 34 defines a valve cylinder 13 which extends from the top end 34a of said cylindrical wall 34 down to a bottom end 20 that opens out in the bottom of the body 1. The bottom end 20 of the valve cylinder 13 is advantageously fitted with a filter 21 that prevents dust or impurities from penetrating into the valve cylinder 13. The filter 21 may be any kind of foam filter, and preferably creates only a small amount of head loss between the valve cylinder 13 and the atmosphere. It may be fixed to the body 1 by any means: by adhesive, by clamping using a ring that is screwed or welded to the body 1, etc.

A valve piston 12 slides in sealed manner inside the valve cylinder 13, the valve piston 12 being connected to the web if of the pump piston 13 by a rod 12a. The valve piston 13 has a face 12b that faces downwards, and a face 12a that faces upwards, and that is in contact with the pump chamber 8.

Figure 3:
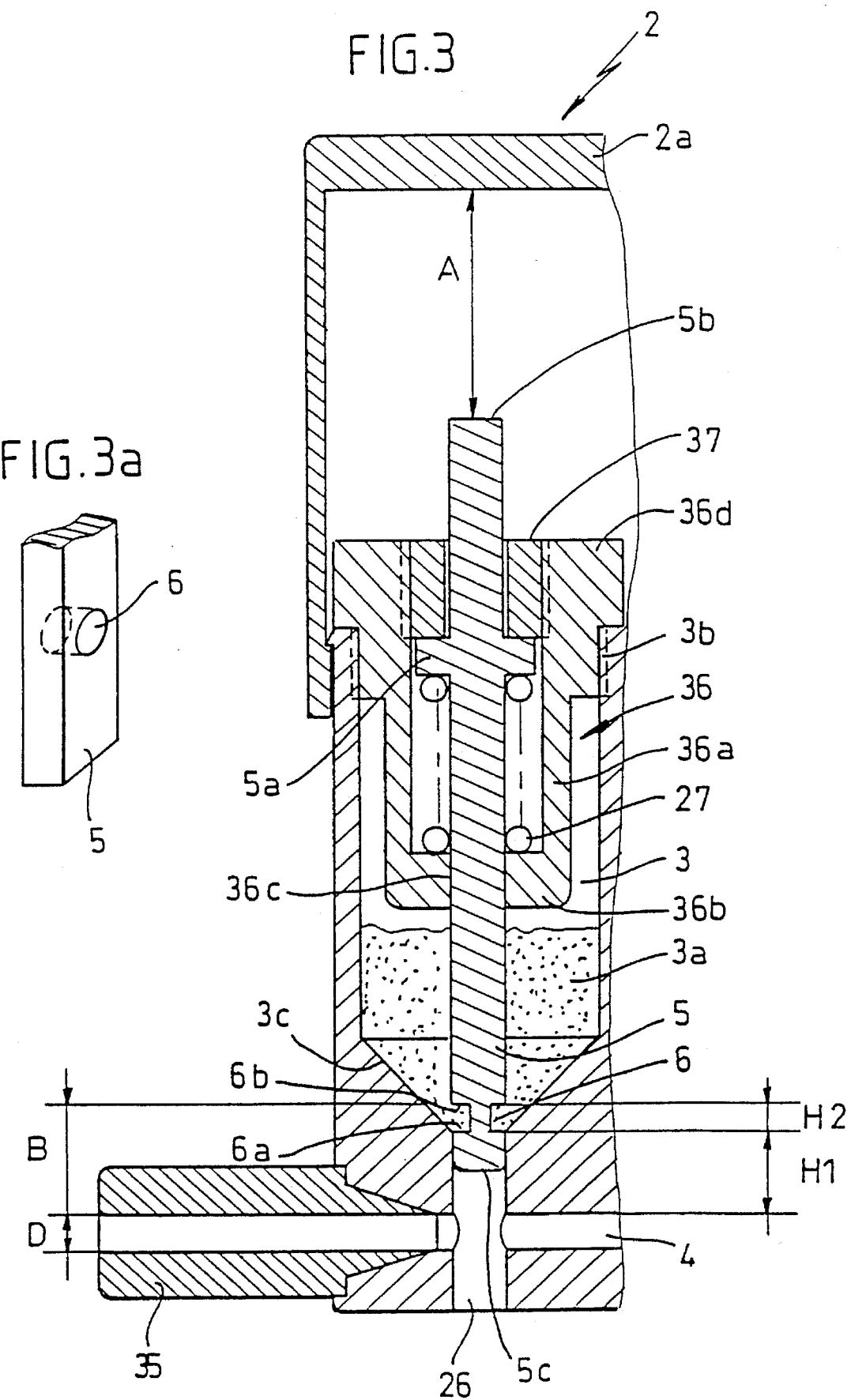
FIG. 3 is a fragmentary view showing the lefthand portion of FIG. 1.

When a user actuates a device as shown in FIGS. 1 to 3 by actuating the pusher 2, the pusher 2 moves down from its rest position to an "actuated" position which is constituted by the bottom abutment position of the pusher 2. When the pusher is in its "actuated" position, the valve piston 12 is close to the filter 21, as shown in dashed lines in FIG. 2. A lateral outlet orifice 14 is formed through the valve cylinder 13 immediately above the position occupied by the top face 12c of the valve piston 12 when the pusher is in its actuated position. As shown in FIG. 2, the outlet orifice 14 causes the valve cylinder 13 to communicate with the ejection channel 4.

Thus, when the pusher 2 is actuated, the content of the pump chamber 8 is compressed, thereby closing the inlet valve, after which the air contained in the pump chamber 8 is compressed until the face 12c of the valve piston has disengaged the lateral outlet orifice 14. The air contained in the pump chamber then escapes through said lateral orifice. In this actuated position, the notches 34b guarantee that the web 9f of the piston does not come into sealed contact with the top end 34a of the wall 34, and thus it guarantees that the compressed air contained in the pump chamber 8 can escape freely via the lateral outlet orifice 14. It may also be observed that the bottom end 20 of the valve cylinder 13 forms a vent which prevents a puff of air being created in the ejection channel prior to the compressed air being expelled from the pump chamber 8, and which also prevents a volume of air contained in the valve cylinder 13 being compressed after the bottom face 12b of the valve piston has gone past the lateral outlet orifice 14 since that could possibly impede the movement of the device as a whole.

When the pusher 2 is released, the return spring of said pusher 2 returns the pump piston 9 to its initial position. During this movement, the top face of the valve piston moves back above the lateral outlet orifice 14 so the pump chamber 8 is isolated and suction is established in the pump chamber 8, thereby opening the inlet valve of the pump. The pump chamber fills up again with air until the pusher 2 has returned to its rest position.

FIG. 3 shows the powder storage and feed means of the FIG. 1 device. The powder supply 3 is constituted by a housing formed in the body 1, extending between a top end 3b and a funnel-shaped bottom end 3c. The bottom end 3c of the supply 3 is extended vertically downwards by a feed channel 26 which intersects the ejection channel 4 perpendicularly, and which opens out in the bottom of the body 1. Between the bottom end 3c of the supply 3 and the ejection channel 4, the feed channel 26 extends over a height H1.

In the open top end 3b of the supply 3, there is mounted a cup 36 which has a side wall 33 that extends vertically between an open top end 36d and a bottom 36b. The bottom 36b includes a central orifice 36c. The cup 36 is mounted in the top end 3b of the supply 3 by any known means, e.g. by a force-fit, by engagement and welding, or by screwing. In the example shown in FIG. 3, the top end 3b is threaded on the inside while an outside portion of the cup 36 is threaded on the outside, the cup 36 thus being screwed into the top end 3b of the supply 3.

A feed rod 5, which is optionally of circular section, is slidably mounted in the orifice 36c of the cup and in the vertical feed channel 26. The rod 5 extends vertically between a top end 5b and a bottom end 5c. The top end 5b projects above the top end 36d of the cup 36 while the device is in its rest position as shown in FIG. 3, and the bottom end 5c of the feed rod is engaged in the feed channel 26 when the device in its rest position. The rod 5 also includes a collar 5a disposed inside the side wall 36a of the cup 36. A compression spring 26 is mounted between the collar 5a and the bottom 36b of the cup 36, urging the feed rod 5 upwards, i.e. towards the pusher 2. An abutment sleeve 37 is mounted inside the top end 36b of the cup 36 so as to limit upward movement of the feed rod 5. The sleeve 37 may be fixed to the cup 36 by any known means, e.g. by engagement followed by ultrasound welding, or by screwing, as shown in FIG. 3.

The feed rod 5 also includes a measuring recess 6 which, in the example shown in FIG. 3, is an annular recess formed in the periphery of the rod 5. The recess 6 extends vertically between a bottom shoulder 6a and a top shoulder 6b over a height H2 which is less than H1.

When the pusher 2 is actuated, it begins by travelling along a certain stroke A before its top wall 2a meets the top wall 5b of the feed rod 5. Thereafter, the top wall 2 of the pusher 2a drives the feed rod 5 downwards against the thrust from the spring 27. The measuring recess 2 is thus driven towards the feed channel 26. The measuring recess 6 is surrounded by powder 3a while it is in the supply 3, and it is therefore filled with powder 3a. When it penetrates into the feed channel 26, the measured quantity of powder that it contains is isolated both from the supply 3 and from the ejection channel 4 because the height H2 of the recess is less than the height H1. Thereafter the recess penetrates into the ejection channel 4 so that the measured quantity of powder in the recess 6 is no longer retained in said recess 6. The height H2 of the recess 6 is preferably less than or equal to the diameter or height D of the ejection channel 4. As a result, the recess 6 can penetrate fully into the ejection channel 4. The length of the rod 5 is designed in such a manner that the recess 6 is fully within the ejection channel 4 when the pusher 2 reaches its actuated position and a puff of compressed air is created in the ejection channel 4 by the air pump 7. If the distance between the channel 4 and the bottom shoulder 6b which defines the measuring recess 6 is written B, and if the vertical distance between the top face 12c of the valve piston 12 and the lateral outlet orifice 14 of the valve cylinder is written C, said lateral outlet orifice generally having a small diameter, then the distance A+B is preferably substantially equal to the distance C.

In the actuated position, the bottom end 5c of the feed rod penetrates into the bottom portion of the channel 26, i.e. into the portion of the channel 26 that is situated beneath the ejection channel 4. Since the rod 5 slides in sealed manner in the channel 26, the ejection channel 4 does not communicate either with the bottom portion or with the top portion of the channel 26 when the pusher 2 is in its actuated position.

Thus, when the pusher 2 reaches its actuated position, and the pump 7 creates a puff of compressed air in the ejection channel 4 going towards the endpiece 35, the puff of compressed air expels the powder contained in the measuring recess 6 and entrains it to the outside, i.e. in the present case, into the mouth or the nose of a patient.

The shape of the measuring recess 6 could be other than annular. For example, as shown in FIG. 3a, the measuring recess 6 could be a hole that is cylindrical or possibly conical and flared towards the endpiece 35, the hole being pierced through the feed rod 5 parallel to the ejection channel 4. In FIG. 3a, the feed rod 5 is rectangular in section, however that is not limiting, and in particular the section of the rod 5 could be circular.

Figure 5:
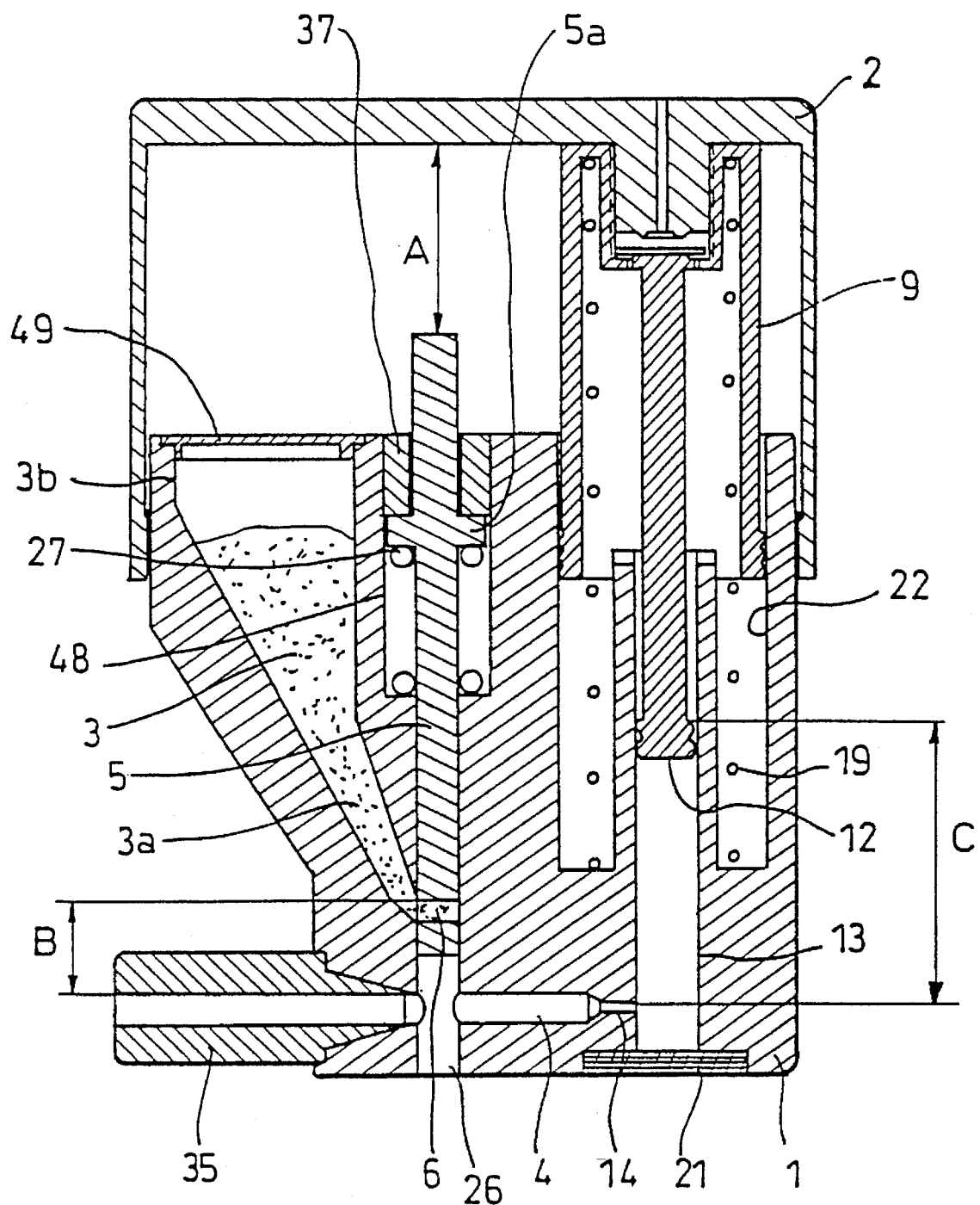
FIG. 5 is a diagrammatic view in longitudinal vertical section through a variant of the device of FIG. 1.

FIG. 5 shows a variant of the FIG. 1 device that is not described in greater detail herein since it operates in the same manner. Unlike the FIG. 1 device, the feed rod 5 does not pass through the supply 3 of powder. The feed channel 26 extends upwards to a housing 48 which receives the return spring 27 for the rod 5, and in which the sleeve 37 is fixed that serves as the abutment for the collar 5a of the rod. The supply 3 has a cover 49 at its top end, and its bottom end 3a forms a duct that slopes towards the channel 26, and that communicates with the channel 26 in the position occupied by the measuring recess 6 when the pusher 2 is at rest. The recess 6 is constituted in this case, by a hole that is parallel to the ejection channel 4. This variant is particularly suitable for powders that are not liable to clumping, for example microgranules.

FIG. 6 shows another variant of the FIG. 5 device in which the supply of powder 3 is no longer disposed at the front of the device, but to one side. The measuring recess 6 is a straight groove extending parallel to the ejection channel 4 and formed in one side only of the feed rod 5. The ejection channel 4 is offset laterally relative to the rod 5 so that the rod 5 penetrates into part only of the ejection channel 4. When the pusher 2 is in its actuated position (down), the measuring groove 6 is fully within said ejection channel 4 so that the powder it contains is entrained by the puff of compressed air then travelling along the ejection channel 4, as produced by an air pump (not shown) identical to that of FIGS. 1 and 5.

Figure 4:
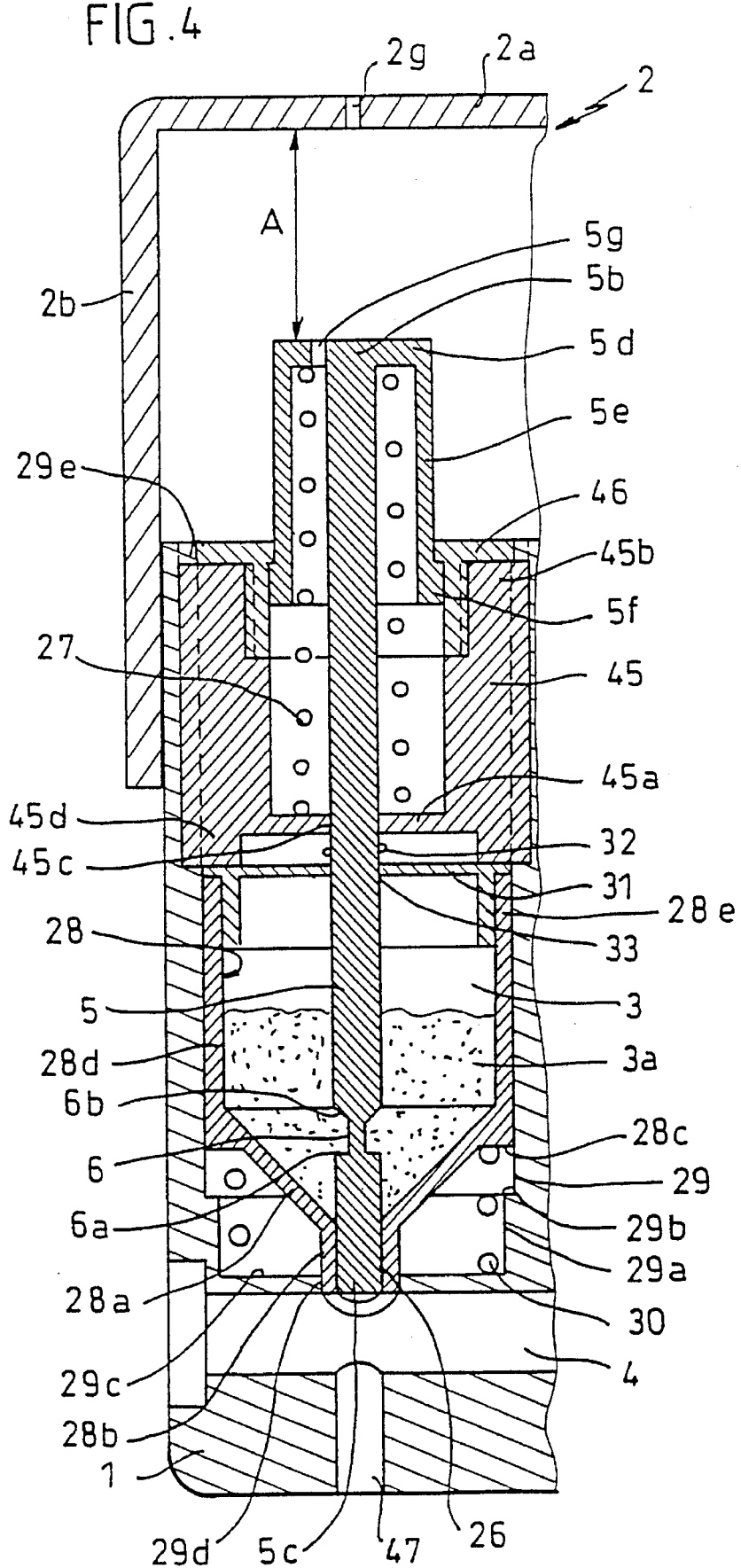
FIG. 4 is a view showing a variant of the lefthand portion of FIG. 1.

A variant of the system in the FIG. 1 device for feeding a measured quantity is shown in detail in FIG. 4. As in the example of FIGS. 1 to 3, a measured quantity of powder is moved from the supply 3 to the ejection channel 4 by means of a feed rod 5 slidably mounted relative to the body 1. As before, the rod 5 includes a measuring recess 6 which is annular in this case and extends between a bottom shoulder 6a and a top shoulder 6b of the rod 5. In the particular case shown in FIG. 4, the top shoulder 6b is not radial, but forms an open angle, e.g. substantially equal to 135° relative to the narrow portion of the rod situated beneath it.

Unlike the example of FIGS. 1 to 3, the supply of powder 3 is not directly constituted by a housing in the body 1, but is constituted by an enclosure 28 slidably mounted in a cylindrical housing 29 of the body 1. The housing 29 extends between an open top end 29e and a bottom 29c. The bottom 29c is pierced by an orifice 29d which communicates with the ejection channel 4. In addition, the housing 29 includes a bottom portion 29a of slightly smaller diameter defining an annular shoulder 29b facing upwards.

The enclosure 28 has a cylindrical wall 28b which slides in the housing 29. The cylindrical wall 28d extends between a top end 28e and a bottom end that is extended downwards by a conical wall 28a, which is itself extended downwards by a cylindrical wall 28d that defines a feed channel 26. The cylindrical wall 28b slides in sealed manner in the orifice 29d so that it can penetrate, at least in part, into the ejection channel 4 when the enclosure 28 slides in its housing 29. In addition, the enclosure 28 includes a downwardly-facing annular bearing surface 28c on its outside. A helical compression spring 30 is mounted between the bottom 29c of the housing 29 and the bearing surface 29c in such a manner as to urge the enclosure 28 upwards. In addition, the bearing surface comes into abutment against the shoulder 29b when the enclosure is moved far enough downwards so that the shoulder 29 defines a bottom abutment for the enclosure 28.

The open top end 28e of the enclosure 28 is closed by a cover 31 which is fixed by any known means and which includes a central orifice 33.

A cup 45 which includes a side wall extending axially between an open top end 45b and a bottom end 45d is mounted in the open top end 29e of the housing 29, e.g. by being screwed therein. The cup 45 includes a bottom 45a situated above the bottom end 45d. The bottom 45a is pierced by a central orifice 45c. In addition, a sleeve 46 is mounted in the open top end 45b of the cup 45, e.g. by being screwed therein. The feed rod 5 extends vertically between a bottom end 5c and a top end 5b. In the rest position of the pusher, as shown in FIG. 4, the bottom end 5c of the rod slides in sealed manner in the feed channel 26 of the enclosure 28. The top end 5b of the rod includes a radial wall 5d which is pierced in this case by a vent orifice 5g and that is extended vertically downwards by a cylindrical wall 5e to a bottom end provided with an outer rim 5f. The return spring 26 of the feed rod 5 is disposed between the bottom 45a of the cup 45 and the radial wall 5d of the rod 5. The return spring 27 urges the rod 5 upwards and the upward stroke of the rod 5 is limited by the outer rim 5f coming into abutment against the sleeve 46.

The body 1 also includes a vertical channel 47 which extends in line with the rod 5 between the ejection channel 4 and the bottom edge of the body 1.

Finally, the rod 5 slides in the orifice 33 of the cover 31 with little clearance, and in any event with clearance that is small enough to prevent the powder contained in the enclosure 28 being capable of escaping via the orifice 33. Also, the rod 5 includes at least one lateral stud 32 which, when the device is in its rest position as shown in FIG. 4, lies between the bottom 45a of the cup 45 and the cover 31.

When a user presses down the pusher 2, the top wall 2a of the pusher 2 initially travels along a certain stroke A before coming into contact with the top end 5b of the feed rod 5a. Thereafter, continued depression of the pusher 2 entrains the feed rod downwards. The studs 32 therefore encounter the cover 31 and as a result they entrain the enclosure 28 downwards against the force of the spring 30. During this movement, the cylindrical wall 28b of the enclosure 28 slides in sealed manner in the orifice 29d and penetrates into the ejection channel 4. As soon as the bearing surface 28c comes into abutment against the shoulder 29b, movement of the enclosure 28 stops. As a result, the studs 32 are forced through the orifice 33 of the cover 31. This forced passage may be achieved by the studs 32 being somewhat flexible, or possibly by the cover 31 being somewhat flexible.

From this instant, the spring 30 imparts a sudden upwards movement to the enclosure 28 until the cover 31 bangs against the bottom end 45d of the cup 45. At this moment, the bottom shoulder 6a of the measuring recess 6 is substantially at the bottom end of the conical wall 28a so that the sudden movement and the shock imparted to the enclosure 28 cause the powder 3a contained in the enclosure 28 to be put into suspension. Consequently, any clumps in the powder 3a are broken up so the powder fills the measuring recess 6 properly.

Thereafter, the feed rod 5 continues its downward movement, but now sliding in the feed channel 26 which performs the same function as in the device of FIGS. 1 to 3. When the measuring recess 6 is fully in the ejection channel 40, the pusher 2 is in its pushed-down position, i.e. in its actuated position, and the compressed air contained in the pump chamber 8 is ejected in the manner explained above. In this way, the quantity of powder contained in the annular measuring recess 6 is expelled via the ejection channel 4 under the effect of the puff of compressed air coming from the pump chamber.

When the user releases the pusher 2, the pusher returns to its rest position under drive from its return spring 19, and the feed rod 5 returns to its rest position under drive from the spring 27. During this movement, the studs 32 are forced back through the orifice 33 under drive from the spring 27.

As shown in dashed lines in FIG. 4, a flexible membrane 50 may optionally be fixed in sealed manner to the rod 5 and to the cover 31 or the enclosure 28 to improve sealing between the cover 31 and the rod 5.

In all embodiments, it is possible for the feed rod 5 to be secured to the pusher or to be placed in contact with the pusher, by adapting the disposition of the rod 5 and/or the diameter of the pump piston.

I claim:

1. A device for projecting measured quantities of a fluid substance by means of a puff of compressed air, said device comprising:

a body (1) having an ejection channel (4);

an actuator member (2) displaceable relative to the body (1) between a rest position and an actuated position;

a resilient return member (19) for the actuator member, urging the actuator member (2) towards its rest position;

a supply (3) of said substance;

feed means (5, 6) adapted to displace a measured quantity of said substance from the supply (3) into the ejection channel (4) when the actuator member (2) is displaced from its rest position to its actuated position; and an air pump (7) having a pump chamber (8) provided with a displaceable wall (9) secured to the actuator member (2) and adapted to compress the pump chamber (2) when the actuator member is displaced from its rest position to its actuated position, said pump chamber (8) having an inlet valve (10, 11) which communicates with the atmosphere, and an outlet valve (12, 13, 14) which communicates with the ejection channel (4), the outlet valve being constituted by a shutter member (12) which co-operates with an outlet opening (14), said shutter member (12) isolating the outlet opening (14) from the pump chamber (8) so long as the actuator member (2) is not in the immediate vicinity of its actuated position, said shutter member (12) opening communication between the pump chamber (8) and the outlet opening (14) when the actuator member (2) is in the immediate vicinity of its actuated position;

the device being characterized in that the outlet valve is constituted by a valve piston (12) constrained to move with the actuator member (2) and sliding in sealed manner in a valve cylinder (13) having a top end (13a), said cylinder having a lateral outlet orifice (14) which communicates with the ejection channel (4), said valve cylinder having its top end in communication with the pump chamber (8), said lateral outlet orifice being positioned sufficiently far from said top end of the valve cylinder for the valve piston (12) to isolate the lateral outlet orifice (14) from the pump chamber so long as the actuator member (2) is not in the immediate vicinity of its actuated position.

2. A device according to claim 1, in which the valve cylinder (13) possesses a vent orifice (20) positioned in such a manner that said lateral outlet orifice (14) is disposed between said vent orifice and said top end of the valve cylinder which is in communication with the pump chamber (8).

3. A device according to claim 2, in which said vent orifice (20) is provided with a filter (21) to prevent dust penetrating into the valve cylinder.

4. A device according to claim 1, in which the feed means (5, 6) are constituted by a feed rod (5) having a measuring recess (6) at an intermediate position along its length, the feed rod not being secured to the actuator member (2), said feed rod being urged towards an abutment position by resilient means (27) and the actuator member travelling along a certain stroke (A) from its rest position before pushing said rod against the action of the resilient means (27) of the feed rod.

5. A device according to claim 4, in which the measuring recess is annular in shape and is located within the ejection channel when the actuator member is in its actuated position.

6. A device according to claim 1, in which the feed rod (5) slides in the supply (3) of substance to be projected, said supply (3) is an enclosure (28) that slides with lost motion parallel to the feed rod (5) in a housing (29) of the body (1), resilient means (30) urging said enclosure (28) away from the ejection channel (4), the enclosure possessing a wall (31) remote from the ejection channel (4), which wall includes an orifice (33) through which the feed rod (5) passes, the feed rod (5) including a lateral projection (32) that is outside the enclosure (28) when the actuator member (2) is in its rest position, said lateral projection (32) interfering with said wall (31) of the enclosure by displacing the enclosure a certain distance against the urging of the resilient means (30) of the enclosure when the actuator member (2) is displaced towards its actuated position, and said lateral projection (32) is sufficiently flexible to retract resiliently as it passes through said orifice (33) of said wall (31) of the enclosure once sufficient axial force is exerted by said lateral projection (32) on said wall (31) of the enclosure.

7. A device according to claim 1, in which the feed rod (5) slides in the supply (3) of substance to be projected, said supply (3) is an enclosure (28) that slides with lost motion parallel to the feed rod (5) in a housing (29) of the body (1), resilient means (30) urging said enclosure (28) away from the ejection channel (4), the enclosure possessing a wall (31) remote from the ejection channel (4), which wall includes an orifice (33) through which the feed rod (5) passes, the feed rod (5) including a lateral projection (32) that is outside the enclosure (28) when the actuator member (2) is in its rest position, said lateral projection (32) interfering with said wall (31) of the enclosure by displacing the enclosure a certain distance against the urging of the resilient means (30) of the enclosure when the actuator member (2) is displaced towards its actuated position, and said wall (31) of the enclosure (28) which is remote from the ejection channel is sufficiently flexible to deform elastically so as to allow the lateral projection (32) of the feed rod to pass through the orifice (33) of said wall (31) when sufficient axial force is exerted by said lateral projection (32) on said wall (31) of the enclosure.

* * * * *